US00PP35220P2

(12) United States Plant Patent
Vandenberg

(10) Patent No.: US PP35,220 P2
(45) Date of Patent: Jun. 13, 2023

(54) ***HIBISCUS* PLANT NAMED 'PINK FLAMINGO WIND'**

(50) Latin Name: *Hibiscus rosa-sinensis*
Varietal Denomination: Pink Flamingo Wind

(71) Applicant: Cornelis P. Vandenberg, Fort Myers, FL (US)

(72) Inventor: Cornelis P. Vandenberg, Fort Myers, FL (US)

(73) Assignee: ARIS HORTICULTURE, INC., Barberton, OH (US)

( * ) Notice: Subject to any disclaimer, the term of this patent is extended or adjusted under 35 U.S.C. 154(b) by 12 days.

(21) Appl. No.: 17/863,376

(22) Filed: Jul. 12, 2022

(51) Int. Cl.
*A01H 6/60* (2018.01)
*A01H 5/02* (2018.01)

(52) U.S. Cl.
USPC ..... Plt./257

(58) Field of Classification Search
USPC ..... Plt./257
See application file for complete search history.

*Primary Examiner* — Annette H Para
(74) *Attorney, Agent, or Firm* — C. Anne Whealy

(57) ABSTRACT

A new and distinct cultivar of *Hibiscus* plant named 'Pink Flamingo Wind', characterized by its semi-upright and uniformly mounded plant habit appropriate for container production; freely branching habit, dense and bushy appearance; glossy dark green-colored leaves; uniform, freely and early flowering habit; single pink-colored flowers with red-colored throats; good postproduction and garden performance; and tolerance to Bacterial Leaf Spot.

2 Drawing Sheets

Figure 1:
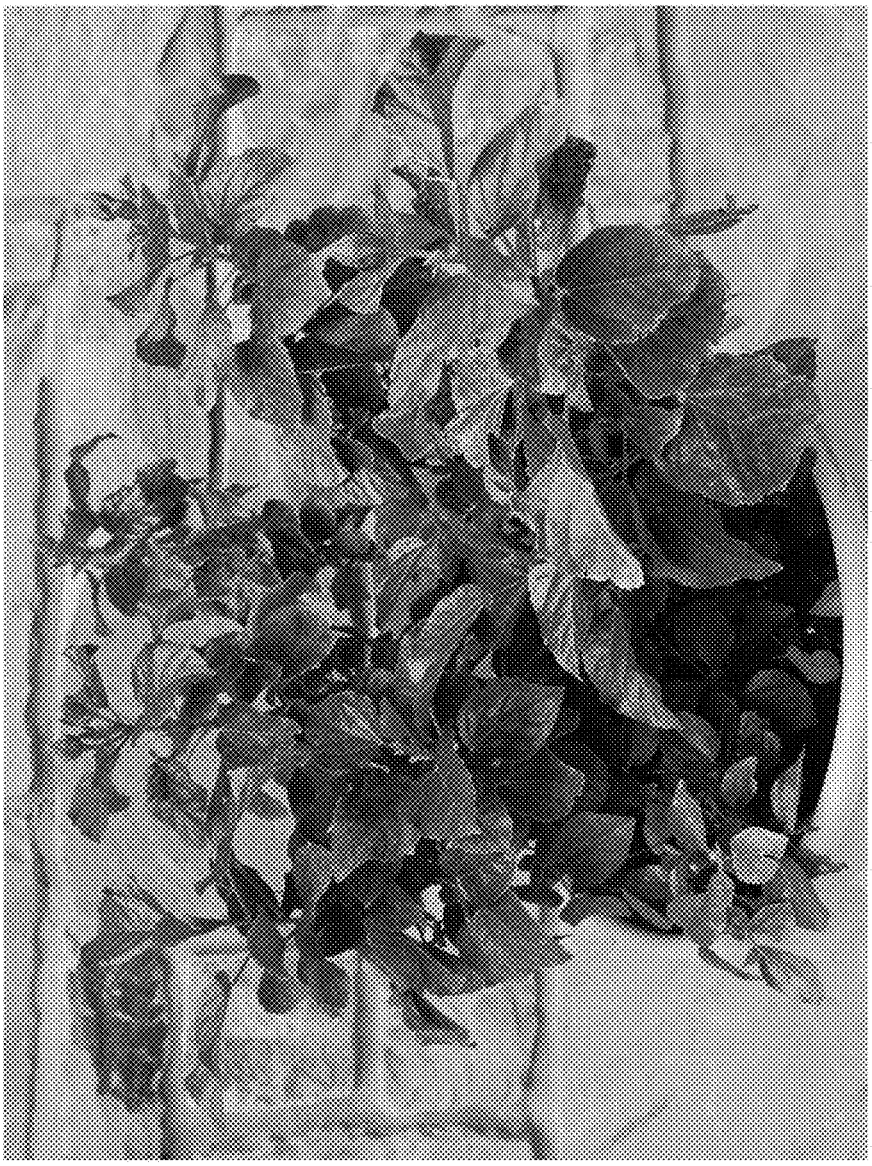

Botanical designation: *Hibiscus rosa-sinensis.*
Cultivar denomination: 'PINK FLAMINGO WIND'.

CROSS-REFERENCED TO CLOSELY-RELATED APPLICATIONS

Title: *Hibiscus* Plant Named 'Pink Punch Wind'
Inventor/Applicant: Cornelis P. Vandenberg
Ser. No. 17/863,378

BACKGROUND OF THE INVENTION

The present invention relates to a new and distinct *Hibiscus* plant, botanically known as *Hibiscus rosa-sinensis* and hereinafter referred to by the name 'Pink Flamingo Wind'.

The new *Hibiscus* plant is a product of a planned breeding program conducted by the Inventor in Alva, Fla. The objective of the breeding program is to create new freely-branching *Hibiscus* plants with uniform plant habit appropriate for container production, early and freely flowering habit, desirable flower color, good garden performance and resistance to Bacterial Leaf Spot.

The new *Hibiscus* plant originated from a cross-pollination made by the Inventor in Alva, Fla. in 2014 of *Hibiscus rosa-sinensis* 'Cayman Wind', disclosed in U.S. Plant Pat. No. 23,760, as the female, or seed, parent with *Hibiscus rosa-sinensis* 'Luau Pink Kai', not patented, as the male, or pollen, parent. The new *Hibiscus* plant was discovered and selected by the Inventor as a single flowering plant within the progeny of the stated cross-pollination in a controlled greenhouse environment in Alva, Fla. on Aug. 19, 2015.

Asexual reproduction of the new *Hibiscus* plant by vegetative terminal cuttings in a controlled greenhouse environment in Alva, Fla. since November, 2015 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pink Flamingo Wind'. These characteristics in combination distinguish 'Pink Flamingo Wind' as a new and distinct *Hibiscus* plant:

1. Semi-upright and uniformly mounded plant habit appropriate for container production.
2. Freely branching habit, dense and bushy appearance.
3. Glossy dark green-colored leaves.
4. Uniform, freely and early flowering habit.
5. Single pink-colored flowers with red-colored throats.
6. Good postproduction and garden performance.
7. Tolerance to Bacterial Leaf Spot.

Plants of the new *Hibiscus* can be compared to plants of the female parent, 'Cayman Wind'. Plants of the new *Hibiscus* differ primarily from plants of 'Cayman Wind' in the following characteristics:

1. Plants of the new *Hibiscus* are more upright than and not as spreading as plants of 'Cayman Wind'.
2. Plants of the new *Hibiscus* flower later than plants of 'Cayman Wind'.
3. Flowers of plants of the new *Hibiscus* are lighter pink in color than flowers of plants of 'Cayman Wind'.
4. Plants of the new *Hibiscus* are more tolerant to Bacterial Leaf Spot than plants of 'Cayman Wind'.

Plants of the new *Hibiscus* can be compared to plants of the male parent, 'Luau Pink Kai'. Plants of the new *Hibiscus* differ primarily from plants of Luau Pink Kai' in the following characteristics:

1. Plants of the new *Hibiscus* are more uniform in plant habit than plants of 'Luau Pink Kai'.
2. Plants of the new *Hibiscus* are more freely branching than plants of 'Luau Pink Kai'.
3. Plants of the new *Hibiscus* are more freely flowering than plants of 'Luau Pink Kai'.
4. Plants of the new *Hibiscus* have better garden performance than plants of 'Luau Pink Kai' are pink in color.
5. Plants of the new *Hibiscus* are more tolerant to Bacterial Leaf Spot than plants of 'Luau Pink Kai'.

Plants of the new *Hibiscus* can be compared to plants of *Hibiscus rosa-sinensis* 'Pink Punch Wind'. Plants of the new *Hibiscus* differ primarily from plants of Pink Punch Wind' in the following characteristics:

1. Plants of the new *Hibiscus* are not as freely flowering as plants of 'Pink Punch Wind'.
2. Plants of the new *Hibiscus* have larger flowers than plants of 'Pink Punch Wind'.
3. Flowers of plants of the new *Hibiscus* are lighter pink in color than flowers of plants of 'Pink Punch Wind'.

Plants of the new *Hibiscus* can also be compared to plants of the *Hibiscus rosa-sinensis* 'Pink Versicolor', not patented. In side-by-side comparisons plants of the new *Hibiscus* differ from plants of 'Pink Versicolor' in the following characteristics:

1. Flowers of plants of the new *Hibiscus* are lighter pink in color than flowers of plants of 'Pink Versicolor'.
2. Flowers of plants of the new *Hibiscus* are smaller than flowers of plants of 'Pink Versicolor'.
3. Plants of the new *Hibiscus* are more tolerant to Bacterial Leaf Spot than plants of 'Pink Versicolor'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet (FIG. 1) is a side perspective view of typical budded plants of 'Pink Flamingo Wind' grown in a container.

Figure 2:
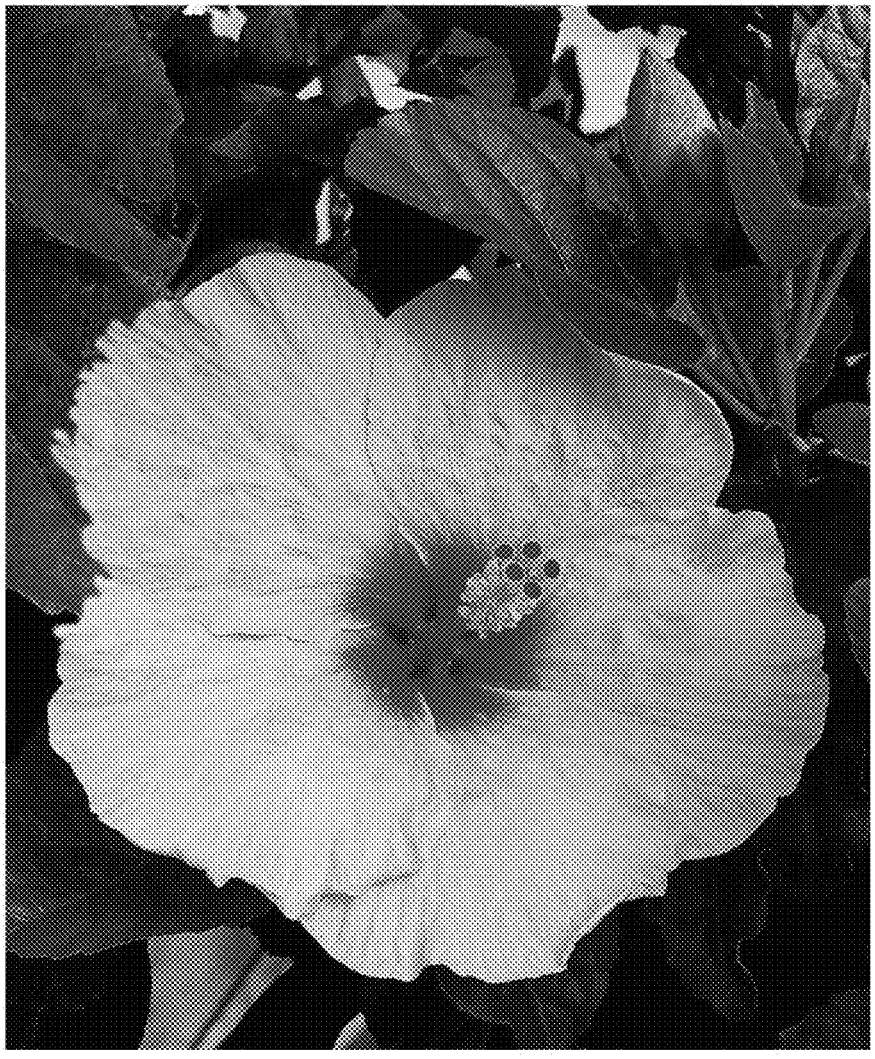

The photograph on the second sheet (FIG. 2) is a close-up view of a typical flower and developed flower bud of 'Pink Flamingo Wind'.

DETAILED BOTANICAL DESCRIPTION

The aforementioned photographs and following observations, measurements and values describe plants grown during the summer in 15-cm containers in a polyethylene-covered greenhouse in Alva, Fla. and in 25-cm containers in an outdoor nursery in Fort Worth, Tex. under cultural practices which closely approximate commercial *Hibiscus* production. During the production of the plants in Texas, day temperatures ranged from 35° C. to 40° C., night temperatures ranged from 24° C. to 35° C. and light levels ranged from 5,000 to 7,500 foot-candles. Plants were pinched two times and were eleven months old when the photographs and the description were taken. In the description, color references are made to The Royal Horticultural Society Colour Chart, 2015 Edition, except where general terms of ordinary dictionary significance are used.

Botanical classification: *Hibiscus rosa-sinensis* 'Pink Flamingo Wind'.

Parentage:

*Female, or seed, parent.*—*Hibiscus rosa-sinensis* 'Cayman Wind', disclosed in U.S. Plant Pat. No. 23,760.

*Male or pollen parent.*—*Hibiscus rosa-sinensis* 'Luau Pink Kai', not patented.

Propagation:

*Type.*—By vegetative terminal cuttings.

*Time to initiate roots, summer and winter.*—About four to five weeks.

*Time to produce a rooted young plant, summer and winter.*—About five to six weeks.

*Root description.*—Thick, fibrous; typically white to light brown in color, actual color of the roots is dependent on substrate composition, water quality, fertilizer, substrate temperature and physiological age of roots.

*Rooting habit.*—Moderate branching; moderately dense.

Plant description:

*Plant form and growth habit.*—Perennial, evergreen, semi-upright and uniformly mounded plant habit; moderately vigorous growth habit.

*Branching habit.*—Freely branching habit with lateral branches potentially develop at every node; pinching enhances lateral branch development; dense and bushy appearance.

*Plant height.*—About 35 cm.

*Plant diameter* (*area of spread*).—About 48 cm.

Lateral branch description:

*Length.*—About 27 cm.

*Diameter.*—About 6 mm.

*Internode length.*—About 1.1 cm.

*Aspect.*—Upright to somewhat outwardly spreading.

*Texture and luster, immature.*—Smooth; somewhat glossy.

*Texture and luster, mature.*—Woody and rough; matte.

*Color, immature.*—Close to 144A.

*Color, mature.*—Close to 199B.

Leaf description:

*Arrangement.*—Alternate, single; numerous; symmetrical.

*Length.*—About 7.25 cm.

*Width.*—About 5.5 cm.

*Shape.*—Ovate.

*Apex.*—Acute.

*Base.*—Truncate, rounded.

*Margin.*—Crenate.

*Texture and luster, upper surface.*—Smooth, glabrous; glossy.

*Texture and luster, lower surface.*—Rough, glabrous; matte to slightly glossy.

*Venation pattern.*—Pinnate; arcuate.

*Color.*—Developing leaves, upper surface: Darker green than 147A. Developing leaves, lower surface: Close to 146A. Fully expanded leaves, upper surface: Darker green than NN137A; midvein, close to 146A and lateral venation, close to NN137A. Fully expanded leaves, lower surface: Close to 146A; midvein, close to 144A and lateral venation, close to 146A.

*Petioles.*—Length: About 3.3 cm. Diameter: About 2.5 mm. Texture and luster, upper and lower surfaces: Smooth, glabrous; slightly glossy. Color, upper and lower surfaces: Close to 144A.

Flower description:

*Flower arrangement and flowering habit.*—Rounded single flowers arranged at terminal leaf axils; uniform and freely flowering habit with about three flowers per terminal; flowers face mostly upright to outwardly.

*Natural flowering season.*—Plants of the new *Hibiscus* flower naturally during the spring and summer or during periods of warm weather; plants flower year-round in the greenhouse.

*Flower longevity.*—Depending on temperature and water status, flowers typically last about two to three days on the plant; flowers persistent.

*Flower diameter.*—About 8.25 cm.

*Flower length* (*height*).—About 7 cm.

*Flower buds.*—Resistance to abscission during shipping: Plants of the new *Hibiscus* have been observed to resist flower bud drop during shipping. Length: About 2.25 cm. Diameter: About 1.2 cm. Shape: Ovoid. Texture and luster: Smooth, glabrous; matte. Color: Close to 146A.

*Petals.*—Arrangement: Corolla consists of a single whorl of five petals that are fused at base; petals imbricate. Length: About 6.25 cm. Width: About 6 cm. Shape: Roughly spatulate. Apex: Rounded to occasionally praemorse; moderately undulate. Base: Attenuate. Margin: Entire; moderately undulate. Texture and luster, upper surface: Smooth, glabrous; velvety; slightly glossy. Texture and luster, lower surface: Glabrous; veins prominent; glossy. Color: When opening and fully opened, upper surface: Close to 65A and 65B. When opening and fully opened, lower surface: Close to 65C and 65D.

*Sepals.*—Appearance: Five sepals in a single whorl fused into a tubular star-shaped calyx. Length: About 2.4 cm. Width: About 9 mm. Shape: Broadly lanceolate. Apex: Sharply acute. Margin: Entire. Texture and luster, upper surface: Smooth, glabrous; waxy; semi-glossy. Texture and luster, lower surface: Smooth, glabrous; matte. Color, upper surface: Close to 146A to 146B. Color, lower surface: More green than 146A.

*Epicalyx.*—Quantity and arrangement: About six to seven in a single whorl fused at base. Length: About 1.4 cm. Width: About 5 mm. Shape: Lanceolate. Apex: Sharply acute. Margin: Entire. Texture and luster, upper surface: Smooth, glabrous; semi-glossy. Texture and luster, lower surface: Smooth, glabrous; matte. Color, upper and lower surfaces: Close to 147A.

*Peduncles.*—Length: About 3.2 cm. Diameter: About 3 mm. Aspect: Upright to slightly outwardly. Strength: Strong, flexible. Texture and luster: Smooth, glabrous; semi-glossy. Color: Close to 144A.

*Reproductive organs.*—Androecium: Stamen number: Numerous, about 30 to 35 per flower. Filament length: About 4 mm. Filament color: Close to 46A. Anther shape: Oblong. Anther length: About 1.5 mm. Anther color: Close to 14A. Amount of pollen: Scarce to moderate. Pollen color: Close to 14A. Gynoecium: Pistil number: One per flower. Pistil length: About 5.5 cm. Style length: About 4.7 cm. Style texture and luster: Smooth, glabrous; waxy; glossy. Style color: Close to 46A. Stigma appearance: Five-parted, rounded. Stigma color: Close to 53A. Ovary color: Close to 11C to 11D.

*Seeds and fruits.*—To date, seed and fruit production has not been observed on plants of the new *Hibiscus*.

Garden performance: Plants of the new *Hibiscus* have been observed to have good garden performance and to tolerate wind, rain and temperatures ranging from about 1° C. to about 40° C.

Pathogen & pest resistance: Plants of the new *Hibiscus* have been observed to be tolerant to Bacterial Leaf Spot (*Pseudomonas cichorii*). To date, plants of the new *Hibiscus* grown under Florida production conditions have not been shown to be resistant to pests and other pathogens common to *Hibiscus* plants.

It is claimed:

1. A new and distinct *Hibiscus* plant named 'Pink Flamingo Wind' as illustrated and described.

* * * * *